United States Patent
Dykstra et al.

(10) Patent No.: US 6,369,250 B1
(45) Date of Patent: Apr. 9, 2002

(54) PROCESS FOR PREPARING AND/OR PURIFYING AMIDO ACID PHENYL ESTER SULFONATES

(75) Inventors: Robert Richard Dykstra, Fairfield; Jeffrey Scott Dupont, Cincinnati; Michael Eugene Burns, Hamilton, all of OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/485,988

(22) PCT Filed: Aug. 13, 1998

(86) PCT No.: PCT/US98/16807

§ 371 Date: Feb. 17, 2000

§ 102(e) Date: Feb. 17, 2000

(87) PCT Pub. No.: WO99/09004

PCT Pub. Date: Feb. 25, 1999

Related U.S. Application Data

(60) Provisional application No. 60/056,594, filed on Aug. 20, 1997.

(51) Int. Cl.$^7$ .............................................. C07C 231/00
(52) U.S. Cl. ........................................ 554/70; 554/68
(58) Field of Search ...................... 554/68, 70

(56) References Cited

U.S. PATENT DOCUMENTS

| | | | |
|---|---|---|---|
| 5,153,541 A | 10/1992 | Johnson et al. ............ | 333/203 |
| 5,286,401 A | 2/1994 | Dung et al. ................ | 252/102 |
| 5,286,879 A | 2/1994 | Letton et al. .............. | 549/231 |
| 5,391,780 A | 2/1995 | Zima et al. ................ | 554/69 |
| 5,414,099 A | 5/1995 | Heinzman et al. .......... | 554/69 |
| 5,466,840 A | 11/1995 | Lutz et al. ................ | 554/70 |
| 5,523,434 A | 6/1996 | Burns et al. ............... | 554/68 |
| 5,534,642 A | 7/1996 | Heinzman et al. .......... | 554/98 |
| 5,650,527 A * | 7/1997 | Lutz et al. ................ | 554/68 |

FOREIGN PATENT DOCUMENTS

| | | | |
|---|---|---|---|
| DE | 3938526 | 5/1991 | |
| EP | 170 386 | 2/1986 | ........... C11D/3/39 |
| EP | 290 292 | 11/1988 | ........... C11D/3/39 |
| EP | 403 152 | 12/1990 | ........... C11D/3/39 |
| JP | 950269630 | 10/1995 | |
| JP | 91/10824 * | 4/1997 | |
| WO | WO 94/10284 | 5/1994 | ........... C11D/2/386 |
| WO | 94/28106 * | 12/1994 | ........... C11D/3/39 |

\* cited by examiner

*Primary Examiner*—Deborah D. Carr
(74) *Attorney, Agent, or Firm*—Richard S. Echler, Sr.; C. Brant Cook; Kim William Zerby

(57) ABSTRACT

The present invention relates to a process for the preparation of a purified salt of 4-sulfophenyl-[(1-oxyalkanoyl)amino] alkanoate. The process comprises the steps of: (a) providing a source of 4-sulfophenyl-[(1-oxyalkanoyl)amino] alkanoate; (b) admixing the source with a water-based purification system to form a purification mixture, the water-based purification system having water present at a ratio of 4-sulfophenyl-[(1-oxyalkanoyl)amino]alkanoate to water ranging from about 1:0.05 to about 1:50, preferably from about 1:0.1 to about 1:40; (c) separating a purified salt of 4-sulfophenyl-[(1-oxyalkanoyl)amino]alkanoate from the purification mixture; and (d) collecting said purified salt of 4-sulfophenyl-[(1-oxyalkanoyl)amino]alkanoate. In preferred embodiments, the purification mixture includes a processin aide such as ethyl alcohol, propyl alcohol, isopropyl alcohol, acetone and mixtures thereof.

31 Claims, No Drawings

PROCESS FOR PREPARING AND/OR PURIFYING AMIDO ACID PHENYL ESTER SULFONATES

This application is a 371 of PCT/US 98/16,807 filed Aug. 13, 1998, which claims benefit of provisional application Ser. No. 60/056,594, filed Aug. 20, 1997.

TECHNICAL FIELD

The present invention relates to a process for preparing and/or purifying amido acid phenyl ester sulfonates. More particularly, the present invention relates to a process for the preparation of purified 4-sulfophenyl-[(1-oxyalkanoyl)amino]alkanoate salts.

BACKGROUND OF THE INVENTION

The synthesis of ingredients for use in low unit cost consumer goods such as laundry detergents, fabric softeners, and the like is of considerable interest to manufacturers. Indeed, the low cost synthesis of ingredients is typically the rate limiting step in the course of bringing a consumer product to the market. Due to the large number of ingredients in consumer goods such as laundry detergents, the expense of individual ingredients must be minimized in order to keep the cumulative product cost within acceptable ranges. The expense associated with the manufacture of consumer goods ingredients is often due to either the cost of the raw materials used to make such ingredients or to the complex reaction and processing chemistry which is required in their manufacture. Accordingly, manufacturers conduct a continuing search for both inexpensive raw materials or simplified reaction sequences.

Amido acid phenyl ester sulfonates form a class of materials which can serve as bleach activators in laundry detergents and other types of bleach-containing cleaning compositions. Such activators have several desirable attributes including excellent bleaching performance with minimal color damage on fabrics dyes, good washing machine compatibility and a good odor profile in the wash. While these materials are potentially obtainable from inexpensive raw materials, the synthesis is somewhat complicated and typically involves the use of solvents. Problems can also arise in the formation of color forming impurities in the end product. Thus, the synthesis of amido acid phenyl ester sulfonates is not straightforward and can be surprisingly problematic.

Processes for the preparation of amido acid phenyl ester sulfonates have been known. U.S. Pat. No. 5,466,840 teaches a 5 step process for the preparation of the compounds. Other processes are disclosed in U.S. Pat. Nos. 5,391,780; 5,414,099; 5,534,642; 5,153,541; 5,650,527; 5,286,879 and 5,523,434.

Accordingly, the need remains for a simple, inexpensive yet effective process for the production of amido acid phenyl ester sulfonates.

SUMMARY OF THE INVENTION

This need is met by the present invention wherein an improved process for preparing a purified amido acid phenyl ester sulfonate is provided. The present invention employs a water-based purification system to remove color forming compounds and other impurities from the amido acid phenyl ester sulfonate. The use of the water-based purification system removes a greater percentage of color forming impurities than the acetic acid based system of the prior art.

The use of the water-based purification system also allows for a greater degree of flexibility to a process for the synthesis of amido acid phenyl ester sulfonate salts due to its ability to purify or crystallize the salt in the presence of large quantities, i.e. greater than 10% and typically more than 20–40%, of the reaction solvent which is required in the synthesis and, thus, eliminates the necessity for a solvent removal step. In addition, the water-based purification system adds flexibility to the synthesis process by providing the ability to work on either a slurry or a homogeneous solution. Accordingly, the purification process of the present invention may be employed on either slurries of crystallized product salt or homogeneous solutions of dissolved product salt which would then allow a controlled recrystallization.

According to a first embodiment of the present invention, a process for the preparation of a purified salt of 4-sulfophenyl-[(1-oxyalkanoyl)amino]alkanoate is provided. The process comprises the steps of:

(a) providing a source of 4-sulfophenyl-[(1-oxyalkanoyl)amino]alkanoate;

(b) admixing the source with a water-based purification system to form a purification mixture, the water-based purification system having water present at a ratio of 4-sulfophenyl-[(1-oxyalkanoyl)amino]alkanoate to water ranging from about 1:0.05 to about 1:50, preferably from about 1:0.1 to about 1:40;

(c) separating a purified salt of 4-sulfophenyl-[(1-oxyalkanoyl)amino]alkanoate from the purification mixture; and (d) collecting the purified salt of 4-sulfophenyl-[(1-oxyalkanoyl)amino]alkanoate.

Preferably, the source of 4-sulfophenyl-[(1-oxyalkanoyl)amino]alkanoate includes a polar aprotic reaction solvent selected from the group consisting of dialkylacetamides, dialkyl sulfoxides, dialkyl ethers of polyethylene glycol and cyclic or acyclic alkyl sulfones and most preferably is tetrahydrothiophene-1,1-dioxide.

The water-based purification system preferably further comprises a processing aide such as one selected from the group consisting of linear or branched $C_1$ to $C_6$ alcohols or diols, linear or branched $C_1$ to $C_6$ ketones, linear or branched $C_1$ to $C_6$ esters, cyclic or acyclic $C_1$ to $C_6$ ethers, linear or branched, cyclic or acyclic $C_1$ to $C_6$ sulfoxides and sulfones and mixtures thereof. Most preferably, the processing aide is selected from the group consisting of ethyl alcohol, propyl alcohol, isopropyl alcohol, acetone and mixtures thereof. In highly preferred scenarios, the processing aide has a density of less than or about that of tetrahydrothiophene-1,1-dioxide and is present at a ratio of 4-sulfophenyl-[(1-oxyalkanoyl)amino]alkanoate to processing aide ranging from about 1:0.1 to about 1:50 and most preferably from about 1:1 to about 1:20. If desired, the step of admixing further comprises the step of heating the purification mixture to a temperature of from about 30° C. to about 100° C.

According to a second embodiment of the present invention, the process for preparing the purified salt of 4-sulfophenyl-[(1-oxyalkanoyl)amino]alkanoate comprises the steps of:

(a) reacting a salt of 4-hydroxybenzene sulfonic acid with a carboxylic anhydride in a reaction solvent to form a reaction mixture having a salt of 4-acyloxybenzenesulfonic acid and a carboxylic acid;

(b) adding a [(1-oxyalkanoyl)amino]alkanoic acid and at least one transesterification catalyst to the reaction mixture and heating at a temperature of from about 120° C. to about 220° C. for from about 0.5 to about 10 hours and a pressure sufficient to maintain reflux of the reaction solvent to form a reaction product containing a salt of 4-sulfophenyl-[(1-oxyalkanoyl)amino] alkanoate;

(c) admixing the reaction product with a water-based purification system to form a purification mixture, the water-based purification system having water present at a ratio of 4-sulfophenyl-[(1-oxyalkanoyl)amino] alkanoate to water ranging from about 1:0.05 to about 1:50;

(d) separating a purified salt of 4-sulfophenyl-[(1-oxyalkanoyl)amino]alkanoate from the purification mixture; and (e) collecting the purified salt of 4-sulfophenyl-[(1-oxyalkanoyl)amino]alkanoate.

According to a third embodiment of the present invention, a process for preparing the purified salt of 4-sulfophenyl-[(1-oxyalkanoyl)amino]alkanoate comprises the steps of:

(a) reacting an alkali metal salt of 4-hydroxybenzene sulfonic acid with a $C_2$ to $C_4$ carboxylic anhydride at a sufficient temperature and time in a reaction solvent to form a reaction mixture having an alkali metal salt of 4-acyloxybenzenesulfonic acid and a $C_2$ to $C_4$ carboxylic acid, wherein the alkali metal salt of 4-hydroxybenezenesulfonic acid and $C_2$ to $C_4$ carboxylic anhydride are present in a mole ratio of 1:1 to 1:40, respectively, and the reaction solvent is present in a weight ratio of 1:1 to 20:1 based on the weight of the alkali metal salt of 4-hydroxybenzenesulfonic acid, provided that excess carboxylic anhydride is removed under reduced pressure from the reaction vessel;

(b) adding a [(1-oxyalkanoyl)amino]alkanoic acid and at least one transesterification catalyst to the reaction mixture and heating to a temperature of from about 120° C. to about 220° C. for from about 0.5 to about 10 hours and a pressure sufficient to maintain reflux of the reaction solvent and to remove the $C_2$ to $C_4$ carboxylic acid from the reaction vessel, to form a reaction product containing a salt of 4-sulfophenyl-[(1-oxyalkanoyl) amino]alkanoate wherein the moles of the [(1-oxyalkanoyl)amino]alkanoic acid added is 0.7 to 5 times the moles of the alkali metal salt of 4-hydroxybenzenesulfonic acid;

(c) admixing the reaction product having reaction solvent and a salt of 4-sulfophenyl-[(1-oxyalkanoyl)amino] alkanoate with a water-based purification system to form a purification mixture, the water-based purification system including a processing aide having water present at a ratio of 4-sulfophenyl-[(1-oxyalkanoyl) amino]alkanoate to water ranging from about 1:0.05 to about 1:50;

(d) separating a purified salt of 4-sulfophenyl-[(1-oxyalkanoyl)amino]alkanoate from the purification mixture;

(e) collecting the purified salt of 4-sulfophenyl-[(1-oxyalkanoyl)amino]alkanoate; and Accordingly, it is an object of the present invention to provide a process for preparing a purified salt of 4-sulfophenyl-[(1-oxyalkanoyl)amino]alkanoate. It is a further object of the present invention to provide a process as above in which a water-based purification system is employed to remove color forming impurities. It is yet another object of the present invention to provide flexibility to a process for preparing a salt of 4-sulfophenyl-[(1-oxyalkanoyl)amino]alkanoate. These, and other objects, features and advantages of the present invention will be recognizable to one of ordinary skill in the art from the following description and the appended claims.

All percentages, ratios and proportions herein are on a weight basis unless otherwise indicated. All documents cited herein are hereby incorporated by reference.

DETAILED DESCRIPTION OF THE PREFERRED EMBODIMENTS

The process of the present invention for preparing purified salts of amido acid phenyl ester sulfonates involves as an important feature a water-based purification system. As earlier noted, it is the use of the water-based purification system with or without processing aide which leads to the benefits and advantages of the present invention.

The process, in general, comprises providing a source of 4-sulfophenyl-[(1-oxyalkanoyl)amino]alkanoate, admixing that source with the water-based purification system and separating a purified product. While the source of 4-sulfophenyl-[(1-oxyalkanoyl)amino]alkanoate may be provided via various means, the preferred source is the in situ preparation of the 4-sulfophenyl-[(1-oxyalkanoyl) amino]alkanoate.

Preparation of 4-sulfophenyl-[(1-oxyalkanoyl)amino] alkanoate

The preparation of the 4-sulfophenyl-[(1-oxyalkanoyl) amino]alkanoate involves two basic steps and is fully described in U.S. Pat. No. 5,466,840, the disclosure of which is herein incorporated by reference. In the first step, a salt, such as an alkali metal salt, of 4-hydroxybenzenesulfonic acid is reacted with a $C_2$ to $C_4$ carboxylic anhydride preferably at a temperature of 50° C. to 200° C. for 0.5 to 5 hours in a reaction solvent to form a reaction mixture having a salt of 4-acyloxybenzenesulfonic acid and a $C_2$ to $C_4$ carboxylic acid. Preferably, the reaction is conducted at a temperature of 110° C. to 170° C. for 1 to 2 hours. Preferably, the salt is an alkali metal salt and may be any alkali metal such as sodium and potassium, or alternatively another salt such as calcium, magnesium or ammonium. However, sodium is the most preferred.

The $C_2$ to $C_4$ carboxylic anhydride is present in an amount of from about 1 to about 40 moles per mole of the salt of 4-hydroxybenzenesulfonic acid, preferably about 1 to about 5 moles, and most preferably about 1 to about 1.5 moles. Examples of suitable $C_2$ to $C_4$ carboxylic anhydrides are acetic anhydride, propionic anhydride, butyric anhydride, and isobutyric anhydride with acetic anhydride being the most preferred.

The reaction solvent for use in the reaction includes polar aprotic solvents such as N,N-dimethylacetamide; dialkyl sulfoxide wherein the alkyl group has one to six carbon atoms such as dimethyl sulfoxide; dimethyl ethers of diethylene glycol such as triglyme; cyclic or acyclic alkyl sulfones wherein the alkyl group has one to six carbon atoms such as tetrahydrothiophene-1,1-dioxide; and halogenated aromatic solvents such as dichlorobenzene and trichlorobenzene; and alkyl substituted aromatic solvents where the alkyl groups contain one to six carbon atoms such as triisopropylbenzene. Preferably, the reaction solvent is tetrahydrothiophene-1,1-dioxide. The reaction solvent is present in a ratio of reaction solvent to the salt of 4-hydroxybenzenesulfonic acid of about 1:1 to about 20:1, preferably about 4:1 to about 6:1 weight ratio.

Upon completion of the formation of a salt of 4-acyloxybenzenesulfonic acid, a transesterification step is performed. This step involves the addition of [(1-oxyalkanoyl)amino alkanoic acid and a transesterification catalyst to the reaction mixture of step one which includes the salt of 4-acyloxybenzenesulfonic acid. The reaction mixture is then heated to a temperature of from about 120° C. to about 220° C. for about 0.5 to about 10 hours and a pressure sufficient to maintain reflux of the reaction solvent and to remove $C_2$ to $C_4$ carboxylic acid from the reaction vessel, to form a product mixture containing a salt of 4-sulfophenyl-[(1-oxyalkanoyl)amino]alkanoate. Preferably, the transesterification reaction is conducted at a temperature of from about 150° C. to about 220° C. for about 2 to about 6 hours. Removal of the co-carboxylic acid can be achieved via distillation or by sparging with an inert gas such as nitrogen. Additional reaction solvent may be added in the transesterification step to maintain a fluid reaction mixture provided it is the same as the reaction solvent employed in the first step. The moles of [(1-oxyalkanoyl) amino alkanoic acid added is about 0.7 to about 5 times the moles of the salt of 4-hydroxybenzenesulfonic acid used in the first step.

The [(1-oxyalkanoyl)amino alkanoic acid is prepared by routes which are well known in the art and disclosed for example in U.S. Pat. Nos. 5,391,780; 5,414,099; 5,534,642; 5,153,541; 5,650,527; 5,286,879 and 5,523,434, the disclosures of which are herein incorporated by reference. A preferred synthesis for the [(1-oxyalkanoyl)amino alkanoic acid is an amidation reaction involving reacting a nitrogen compound selected from a lactam and an amino acid with a carboxylic acid or ester. Preferably, the [(1-oxyalkanoyl) amino alkanoic acid is 6-[(1-oxyoctyl)amino hexanoic acid, 6-[(1-oxynonyl)amino hexanoic acid, 6-[(1-oxydecyl)amino hexanoic acid or mixtures of the three.

Suitable lactam monomers contain at least about 3, more preferably about 4 to about 7 carbon atoms per molecule. Suitable lactam monomers include butyrolactam, valerolactam, epsilon-caprolactam, beta propiolactam, delta valerolactam, and similar lactams. These lactams may be substituted at the nitrogen atom by hydrocarbon radicals containing one to three carbon atoms, for example, methylcaprolactam. Epsilon-caprolactam and suitable derivatives thereof are the preferred lactam monomers.

The amino acid has the general formula $NH_2(CR^1R^2)_m$ COOH and is characterized by the basic amino group ($NH_2$) and an acidic carboxyl group (COOH). m is an integer ranging from about 1 to about 26 and preferably about 1 to about 10. $R^1$ and $R^2$ are independently selected from hydrogen, unsubstituted or substituted straight chain or branched $C_1-C_{20}$ alkyl, unsubstituted or substituted $C_3-C_8$ cycloalkyl, $C_3-C_8$ alkenyl, $C_3-C_8$ alknyl and $C_6-C_{14}$ aryl.

The unsubstituted or substituted $C_3-C_8$ cycloalkyl groups mentioned above refer to cycloaliphatic hydrocarbon groups which contain about 3 to about 8 carbon atoms in the ring, preferably 5 to 6 carbon atoms, and these cycloalkyl groups substituted with one to two of $C_1-C_4$ alkyl, $C_1-C_4$ alkoxy, hydroxy or $C_1-C_4$ alkaneoxy.

The $C_3-C_8$ alkenyl and $C_3-C_8$ alkenyl groups represent straight of branched chain hydrocarbon radicals containing 3 to 8 carbon atoms in the chain and which contain a carbon—carbon double bond or a carbon—carbon triple bond, respectively.

The term "aryl" is used to include carboxylic aryl groups containing up to fourteen carbon atoms, e.g. phenyl and naphthyl and those substituted with one or two groups selected from $C_3-C_4$-alkyl, $C_3-C_4$-alkoxy, $C_3-C_4$-alkoxycarbonyl, $C_1-C_4$-alkaneoxy, $C_1-C_4$-alkanoylamino, halogen, cyano, $C_1-C_4$-alkylsulfonyl, $C_1-C_4$-alkylene-(OH)$_n$, O-$C_1-C_4$-alkylene-(OH)$_n$, S-$C_1-C_4$-alkylene-(OH)$_n$, SO$_2$-$C_1-C_4$-alkylene-(OH)$_n$, CO$_2$-$C_1-C_4$-alkylene-(OH)$_n$, SO$_2$N (R$_3$)$C_1-C_4$-alkylene-(OH)$_n$, SO$_2$N($C_1-C_4$-alkylene-OH)$_2$, CON(R$_3$)$C_1-C_4$-alkylene-(OH)$_n$, CONC$_{1-C4}$-alkylene-(OH)$_2$, N(SO$_2$C$_1-C_4$-alkyl)-alkylene-(OH)$_n$, N(SO$_2$phenyl)-$C_1-C_4$-alkyl)-alkylene-(OH)$_n$ wherein n is one or two.

The term "aryl" is also used to include heterocyclic aryl groups such as a 5 or 6 membered heterocyclic aromatic ring containing one oxygen atom, and/or one sulfur atom, and/or up to three nitrogen atoms and the heterocyclic aryl ring may be optionally fused to one or two phenyl rings or another 5 or 6 membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadizinyl, oxadiazinyl, dithiazinyl, dioxazinyl, oxathiazinyl, tetrazinyl, thiatriazinyl, oxatriazinyl, dithiadiazinyl, imidazolinyl, dihydropyridyl, tetrahydropyridyl, tetrazolo-[1,5b] pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carboxylic aryl hydrocarbon moiety containing up to fourteen carbons, e.g., o-, m- and p-phenylene, and those substituted with one or two groups selected from $C_1-C_4$ alkyl, $C_1-C_4$ alkoxy or halogen.

The carboxylic acid compound is a carboxylic acid or carboxylic acid ester, or combination thereof, which contains an aliphatic, such as a straight or branched chain, or aliphatic radical, cycloaliphatic or hydroaromatic radical. The carboxylic acid or carboxylic acid ester has from about 6 to about 26 carbon atoms, preferably about 8 to about 20 carbon atoms, and most preferably from about 8 to about 10 carbon atoms. These radicals may be connected to the carboxyl group through an aromatic radical. The carboxylic acids and carboxylic acid esters may be straight or branched chain fatty acids of natural or synthetic origin which may be of a saturated or unsaturated nature. The carboxylic acids and esters can contain more than one carboxylic acid or ester group. Esters of carboxylic acids include, but are not limited to the methyl, ethyl, propyl, and butryl ester of a carboxylic acid. The carboxylic acids and carboxylic acid esters may be used in pure form or else in the form of their mixtures.

Suitable examples of carboxylic acids and esters are: Caprylic acid, methyl caprylate, pelargonic acid, methyl pelargonate, capric acid, methyl caprate, isopropyl caprate, undecylic acid, lauric acid, palmitic acid, stearic acid, oleic acid, linoleic acid, behenic acid, teraphthalic acid, dimethyl teraphthalate, phthalic, isophthalic acid, napthene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. Preferred carboxylic acids are capric and capryltic. Preferred carboxylic acid esters are methyl caprate and methyl caprylate.

Transesterification catalysts for use in the present invention are known in the art. Such catalysts include tertiary amine catalysts, alkali metal salts, metallic catalysts, acidic catalysts, and combinations thereof. Specific examples of catalysts for use in the present invention include: dimethyl aminopyridine, imidazole, sodium acetate, sodium hydroxide, and titanium tetraisopropoxide. The transesterification catalyst(s) is added in an amount of about 0.01 to about 0.3 moles per mole of the salt of 4-hydroxybenzenesulfonic acid used in the earlier step.

Upon completion of the transesterification reaction and the formation of the salt of 4-sulfophenyl-[(1-oxyalkanoyl)amino]alkanoate, the reaction solvent may be removed in an optional step. The removal of solvent is accomplished by either by an evaporative process such as distillation or drying, or by crystallization followed by filtration. Removal of the solvent is conducted at low vacuum and at a temperature at which vaporization of the solvent occurs. Preferably, the vacuum range is from about 0.5 absolute to about 100 mm Hg, and the temperature range is from about 120° C. to about 230° C. Preferably, at least about 90% and more preferably at least about 95% of the solvent is removed. Of course, it is important to note that this removal of solvent is entirely optional in the present invention as the water-based purification system may operate in the presence of large amounts of reaction solvent.

The reaction product including the salt of 4-sulfophenyl-[(1-oxyalkanoyl)amino]alkanoate is admixed with a water-based purification system to yield the purified salt of the present invention. The water-based purification system, of course, includes at least a minimum amount of water. However, other ingredients such as processing aids may be included in the system.

The water-based purification system has a minimum amount of water such that the ratio of 4-sulfophenyl-[(1-oxyalkanoyl)amino]alkanoate to water ranges from about 1:0.05 to about 1:50. More preferably, the ratio of salt of 4-sulfophenyl-[(1-oxyalkanoyl)amino]alkanoate to water ranges from about 1:0.1 to about 1:40. As discussed earlier, the reaction solvent does not need to be removed from the reaction product of the salt of 4-sulfophenyl-[(1-oxyalkanoyl)amino]alkanoate synthesis. In such instances, wherein at least about 10%, and more preferably at least about 20% and more preferably at least about 40% of the reaction solvent remains, a lower amount of water is required in the system. In such cases, the ratio of 4-sulfophenyl-[(1-oxyalkanoyl)amino]alkanoate to water preferably ranges from about 1:0.1 to about 1:40. When the reaction solvent is optionally removed as described hereinbefore, a larger percentage of water may be necessary in the purification system. In such instances, the ratio of 4-sulfophenyl-[(1-oxyalkanoyl)amino]alkanoate to water ranges from about 1:1 to about 1:50.

While not wishing to be bound by theory, it is believed that the amount of water used effects product salt recovery and also the amount of color and impurities removed. For highly colored crude reaction products, more water can be used while for less colored products, less water may be employed. The amount of water can also be chosen depending on the particular impurities present. A small amount eliminates select impurities while more water may be required to remove others. In addition, the presence of larger amounts of reaction solvent as defined above allows less water to be employed.

As discussed early, a processing aide may be added to the water-based purification system to, among other reasons, enhance separation and reduce foaming in the process. The processing aide is selected from the group consisting of linear or branched $C_1$ to $C_6$ alcohols or diols, linear or branched $C_1$ to $C_6$ ketones, linear or branched $C_1$ to $C_6$ acids, linear or branched $C_1$ to $C_6$ esters, cyclic or acyclic $C_1$ to $C_6$ ethers, linear or branched, cyclic or acyclic $C_1$ to $C_6$ sulfoxides and sulfones and mixtures thereof Most preferably, the processing aide is selected from the group consisting of methyl alcohol, ethyl alcohol, propyl alcohol, isopropyl alcohol, acetone, acetic acid and mixtures thereof with isopropyl alcohol being the most preferred.

In highly preferred scenarios, the processing aide is miscible with water and has a density of less than or equal to the preferred reaction solvent, tetrahydrothiophene-1,1-dioxide so as to increase the density difference between the product salt and the purification system thereby increasing the ease of removal of the salt. This solvent has a density of 1.216 gm/cm$^3$. The processing aide is typically present in the purification system at a ratio of 4-sulfophenyl-[(1-oxyalkanoyl)amino]alkanoate to processing aide ranging from about 1:0.1 to about 1:50 and most preferably from about 1:1 to about 1:20. The amount of processing aide employed is mainly dependent on the physical properties desired. The lower end can be chosen to minimize foaming (although less is also needed when reaction solvent which also reduces foaming is present). The upper end is typically chosen for convenience during product recovery such as filtering or centrifuging. When a processing aide is used in conjunction with the water-based purification system, product yields from recrystallization are typically greater than about 75%, more preferably 85%, and most preferably 90%.

As discussed earlier, the water-based purification system provides increased flexibility to the prior art processes by allowing recovery of product salt from either a slurry or a homogeneous solution. That is, in a typical process the step of admixing reaction product salt with the purification system with or without processing aide as described hereinbefore yields either a slurry or homogeneous solution of formed product salt. The purification may be conducted on this slurry or homogeneous solution at room or slightly elevated temperatures to remove impurities and color forming bodies. However, the admixing step may also in optional embodiments involve heating the admixture from about 30° C. to about 100° C. to form a slurry or homogenous solution of product salt. The product salt may then be recovered from this homogenous solution or slurry to yield a highly purified product salt. The use of a homogenous solution or slurry provides flexibility and a controlled recrystallization of the product salt to impart various desired results.

The next step of the process involves the separation of the purified salt of 4-sulfophenyl-[(1-oxyalkanoyl)amino]alkanoate from the water-based purification system and any remaining solvent. This separation may be accomplished by methods which are well-known in the art such as centrifugation or filtration. The filtrate from this separation step may include reaction solvent, water and processing aides, if present, which can be individually recovered and recycled to their respective steps. If desired, the purified salt may be dried by any conventional drying technique such as a ring drier or vacuum oven. It is important to note that the purification with the water-based system and separation of the product may be repeated as necessary until a salt of 4-sulfophenyl-[(1-oxyalkanoyl)amino]alkanoate of the desired purity is obtained. Depending upon the purity of the starting materials, greater than about 80% and preferably about 90% yield of product may be obtained in the process of the present invention.

The processes as described herein may be conducted stepwise as a batch process or on a continuous basis. The purified salt of 4-sulfophenyl-[(1-oxyalkanoyl)amino]alkanoate product has the general formula $R^4C(O)N(R^5)(CH_2)_nC(O)$-OBS where $R^4$ represents $C_5$–$C_{21}$ alkyl, $C_5$–$C_{21}$ alkenyl, chlorinated $C_5$–$C_{21}$ alkyl or phenyl that can be substituted by 1 to 3 substituents from among the groups, F, Cl, $SO_3M$, COOM, $C_1$–$C_{21}$ alkyl or $C_2$–$C_{20}$ alkenyl; $R^5$ represents hydrogen or a $C_1$ to $C_3$ alkyl; M represents hydrogen, ammonium, or an alkali metal atom such as sodium or potassium; n is an integer from about 1 to about 8; and -OBS is an oxybenzenesulfonate leaving group. Preferably, the purified salt of 4-sulfophenyl-[(1-oxyalkanoyl)amino]alkanoate is sodium 4-sulfophenyl-6-[(1-oxynonyl)amino]hexanoate, wherein $R^4$ is $C_8H_{17}$, n is 5 and or sodium 4-sulfophenyl-6-[(1-oxydecyl)amino] hexanoate wherein $R^4$ is $C_9H_{19}$, n is 5. The product may also include mixtures of the compounds.

The process of the present invention will be further illustrated by a consideration of the following examples, which are intended to be exemplary of the invention.

EXAMPLE 1

To a mechanically stirred solution of 36 grams of water is added crude reaction product containing 3 grams of crude sodium 4-sulfophenyl-6-[(1-oxynonyl)amino]hexanoate and 6 g of tetrahydrothiophene-1,1-dioxide. The pH is adjusted to 5–6 using sulfuric acid, and the resulting mixture is allowed to warm to 60° C. The solution is allowed to cool to 10° C. over a period of 1–2 hours. The mixture is filtered to obtain a solid salt and a colored filtrate. The solid is washed with 10 grams of water and dried in a vacuum oven at 30° C. (1–5 mm Hg) for 1 hour to give the dried product. Data on the product prior to and after purification is summarized in Table I.

EXAMPLE 2

To a mechanically stirred solution of 3 grams of water and 24 grams of isopropyl alcohol is added crude reaction product containing approximately 3 grams of crude sodium 4-sulfophenyl-6-[(1-oxynonyl)amino]hexanoate and 6 grams of tetrahydrothiophene-1,1-dioxide. The pH is adjusted to 5–6 using sulfuric acid, and the resulting mixture is allowed to warm to 90° C. The solution is stirred for 15 minutes, and the mixture is allowed to cool to 25° C. over a period of 1–2 hours. The mixture is vacuum filtered to obtain a solid and a colored filtrate. The solid is washed with 10 grams of isopropyl alcohol and dried in a vacuum oven at 30° C. (1–5 mm Hg) for 1 hour to give the dried product. Data on the product prior to and after purification is summarized in Table I.

EXAMPLE 3

To a mechanically stirred solution of 2 grams of water and 12 grams of isopropyl alcohol is added crude reaction product consisting of 3 grams of crude sodium 4-sulfophenyl-6-[(1-oxynonyl)amino]hexanoate and 6 grams of tetrahydrothiophene-1,1-dioxide. The pH is adjusted to 5–6 using sulfuric acid, and the resulting mixture is allowed to warm to 65° C. The slurry is stirred for 15 minutes, and the mixture is allowed to cool to 25° C. over a period of 1–2 hours. The mixture is vacuum filtered to obtain a solid and a colored filtrate. The solid is washed 3 times with 6 grams of isopropyl alcohol and dried in a vacuum oven at 30° C. (1–5 mm Hg) for 1 hour to give the dried product. Data on the product prior to and after purification is summarized in Table I.

EXAMPLE 4

To a mechanically stirred solution of 20 grams of water and 120 grams of isopropyl alcohol is added crude reaction product containing a reaction mixture consisting of 30 grams of crude sodium 4-sulfophenyl-6-[(1-oxyoctyl)amino] hexanoate and 60 grams of tetrahydrothiophene-1,1-dioxide. The pH is adjusted to 5–6, and the resulting mixture is allowed to warm to 70° C. The slurry is stirred for 1 hour, and the mixture is allowed to cool to 10° C. over a period of 3 hours. The mixture is centrifuged to obtain a solid and a colored centrate. The solid is reslurried in 25 grams of water and 130 grams of isopropyl alcohol. The resulting mixture is allowed to warm to 75° C. The solution is stirred for 30 minutes, and the mixture is allowed to cool to 10° C. over a period of 2 hours. The mixture is centrifuged to obtain a solid and a colored filtrate. The solid is dried under vacuum to give sodium 4-sulfophenyl-6-[(1-oxyoctyl)amino] hexanoate.

EXAMPLE 5

To a flask equipped with a mechanically stirrer and condenser containing a solution of 3 grams of water and 18 grams of acetone is added crude reaction product consisting of 3 grams of a crude mixture of sodium 4-sulfophenyl-6-[(1-oxynonyl)amino]hexanoate and 6 grams of tetrahydrothiophene-1,1-dioxide. The pH is adjusted to 5–6 using sulfuric acid, and the resulting mixture is allowed to warm to 60° C. The solution is stirred for 15 minutes, and the mixture is allowed to cool to 25° C. over a period of 1–2 hours. The mixture is vacuum filtered to obtain a solid and a colored filtrate. The solid is washed 3 times with 6 grams of acetone and dried in a vacuum oven at 30° C. (1–5 mm Hg) for 1 hour to give the dried product. Data on the product prior to and after purification is summarized in Table I.

EXAMPLE 6

To a magnetically stirred solution of 6 grams of water and 40 grams of acetone is added crude reaction product consisting of 32 grams of crude sodium 4-sulfophenyl-6-[(1-oxynonyl)amino]hexanoate solution composed of 14.5 grams crude sodium 4-sulfophenyl-6-[(1-oxynonyl)amino] hexanoate and 17.6 grams of tetrahydrothiophene-1,1-dioxide. The pH is adjusted to 5–6 using sulfuric acid, and the resulting mixture in a closed vessel is allowed to warm to 90° C. The slurry is stirred for 15 minutes, and the mixture is allowed to cool to 25° C. over a period of 1–2 hours. The mixture is vacuum filtered to obtain a solid and a colored filtrate. The solid is washed with 40 grams of warm acetone and dried in a vacuum oven at 30° C. (1–5 mm Hg) for 1 hour to give the dried product. Data on the product prior to and after purification is summarized in Table I.

EXAMPLE 7

To a mechanically stirred solution of 27 grams of water is added crude reaction product containing a reaction mixture consisting of 3 grams of crude of sodium 4-sulfophenyl-6-[(1-oxynonyl)amino]hexanoate. The pH is adjusted to 5–6 using sulfuric acid, and the resulting mixture is allowed to warm to 60° C. The clear solution is stirred for 15 minutes, and the mixture is allowed to cool to 25° C. over a period of 1–2 hours. The mixture is vacuum filtered to obtain a solid and a colored filtrate. The solid is washed with 13.5 grams of water and dried in a vacuum oven at 30° C. (1–5 mm Hg) for 1 hour to give the dried product. Data on the product prior to and after purification is summarized in Table I.

EXAMPLE 8

To a mechanically stirred solution of 2.5 grams of water and 13 grams of isopropyl alcohol is added 3 grams of crude of sodium 4-sulfophenyl-6-[(1-oxynonyl)amino]hexanoate containing less than 5 wt % of tetrahydrothiophene-1,1-dioxide. The pH is adjusted to 5.5 using sulfuric acid, and the resulting mixture is allowed to warm to 80° C. The clear solution is stirred for 10 minutes, and the mixture is allowed to cool to 25° C. over a period of 1–2 hours. The mixture is vacuum filtered to obtain a solid and a colored filtrate. The solid is washed 3 times with 5 grams of acetone and dried in a vacuum oven at 30° C. (1–5 mm Hg) for 1 hour to give dried sodium 4-sulfophenyl-6-[(1-oxynonyl)amino] hexanoate. Data on the product prior to and after purification is summarized in Table I.

EXAMPLE 9

To a mechanically stirred solution of 3 grams of water and 12 grams of acetone is added 3 grams of a crude reaction product containing sodium 4-sulfophenyl-6-[(1-oxynonyl) amino]hexanoate less than 5 wt % of tetrahydrothiophene-1,1-dioxide. The pH is adjusted to 5.5 using sulfuric acid, and the resulting mixture is allowed to warm to 60° C. The clear solution is stirred for 10 minutes, and the mixture is allowed to cool to 25° C. over a period of 1–2 hours. The mixture is vacuum filtered to obtain a solid and a colored filtrate. The solid is washed 3 times with 5 grams of acetone and dried in a vacuum oven at 30° C. (1–5 mm Hg) for 1 hour to give dried sodium 4-sulfophenyl-6-[(1-oxynonyl) amino]hexanoate. Data on the product prior to and after purification is summarized in Table I.

EXAMPLE 10

To a mechanically stirred solution of 1 grams of water and 6 grams of acetone is added crude reaction product containing 3 grams of crude sodium 4-sulfophenyl-6-[(1-oxydecyl) amino]hexanoate and 6 grams of tetrahydrothiophene-1,1-dioxide. The pH is adjusted to 5–6 using sulfuric acid, and the resulting mixture is allowed to warm to 60° C. In this case, the slurry is stirred for about 10 minutes. The mixture is allowed to cool to room temperature over a period of about 1–2 hours. The mixture is vacuum filtered to obtain a solid and a colored filtrate. The solid is washed 3 times with 12 grams of acetone and dried in a vacuum oven at 30° C. (1–5 mm Hg) for 1 hour to give purified sodium 4-sulfophenyl-6-[(1-oxydecyl)amino]hexanoate. Data on the product prior to and after purification is summarized in Table I.

EXAMPLE 11

A dry 500 mL 3-necked round-bottomed flask equipped with an overhead stirrer (mechanical), condenser with attached Dean Stark apparatus, addition funnel, Argon source, and oil bath with temperature controller is charged with 35.6 g of tetrahydrothiophene-1,1-dioxide and heated to 80° C. To the reaction flask is added 178 mg (2.16 mmol) of sodium acetate, 7.03 g (0.036 mol) of sodium 4-hydroxybenzenesulfonate, and 9.47 g (0.035 mol) of a mixture of 6-[(1-oxynonyl)amino hexanoic acid and 6-[(1-oxydecyl)amino hexanoic acid. The mixture is heated to 140° C. To the reaction is added (via addition funnel) 4.07 mL (0.043 mol) of acetic anhydride over 30–40 min at 140° C. The pressure is then reduced to 15 imm Hg, and as the temperature is raised to 165° C. over a period of 20–30 min, low boiling materials flash over and are collected. The temperature is maintained at about 165° C. (15 mm Hg) for 5 h. After the five hour reaction time, a crude reaction mixture including 4-sulfophenyl-[(1-oxynonyl)amino] hexanoate and 4-sulfophenyl-[(1-oxydecyl)amino] hexanoate is obtained. The crude reaction mixture is transferred to a mechanically stirred solution of 15 grams of water and 60 grams of isopropyl alcohol. The pH is adjusted to 5.5, and the resulting mixture is warmed to 75° C. The solution is stirred and cooled to 25° C. over a period of 3 hours. The mixture is centrifuged to obtain a solid and a colored centrate. The solid is transferred to a mechanically stirred solution of 5 grams of water and 30 grams of isopropyl alcohol, stirred, and centrifuged to obtain a solid which is dried under vacuum to give a mixture of 4-sulfophenyl-[(1-oxynonyl)amino]hexanoate and 4-sulfophenyl-[(1-oxydecyl)amino]hexanoate.

| Experiment | Crude product % | Purified product % | Recovery |
|---|---|---|---|
| 1 | 89.5 | 98.2 | 88% |
| 2 | 89.5 | 98.6 | 94% |
| 3 | 80.3 | 96.2 | 92% |
| 5 | 80.4 | 97.9 | 93% |
| 6 | 36.0 | 93.0 | 99% |
| 7 | 89.5 | 95.1 | 92% |
| 8 | 89.5 | 98.1 | 95% |
| 9 | 80.4 | 96.0 | 97% |

What is claimed is:

1. A process for the preparation of a purified salt of 4-sulfophenyl-[(1-oxyalkanoyl)amino]alkanoate having the formula:

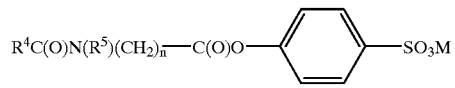

wherein $R^4$ represents $C_5$–$C_{21}$ alkyl, $C_5$–$C_{21}$ alkyl, $C_5$–$C_{21}$ alkenyl, chlorinated $C_5$–$C_{21}$ alkyl or phenyl that can be substituted by 1 to 3 substituents from among the groups, F, Cl, $SO_3M$, COOM, $C_1$–$C_{21}$ alkyl or $C_2$–$C_{20}$ alkenyl; $R^5$ represents hydrogen or a $C_1$–$C_3$ alkyl; M represents hydrogen, ammonium, or an alkali metal atom such as sodium or potassium; n is an integer from about 1 to about 8; and comprising the steps of:
   (a) providing a source of 4-sulfophenyl-[(1-oxyalkanoyl)amino]alkanoate;
   (b) admixing said source with a water-based purification system having water present at a ratio of 4-sulfophenyl-[(1-oxyalkanoyl)amino]alkanoate to water ranging from 1:0.005 to 1:50;
   (c) separating a purified salt of 4-sulfophenyl-[(1-oxyalkanoyl)amino]alkanoate from said purification mixture; and
   (d) collecting said purified salt of 4-sulfophenyl-[(1-oxyalkanoyl)amino]alkanoate.

2. The process as claimed in claim 1 wherein said ratio of 4-sulfophenyl-[(1-oxyalkanoyl)amino]alkanoate to water ranges from about 1:0.1 to about 1:40.

3. The process as claimed in claim 2 wherein said source of 4-sulfophenyl-[(1-oxyalkanoyl)amino]alkanoate includes a polar aprotic reaction solvent selected from the group consisting of dialkylacetamides, dialkyl sulfoxides, dialkyl ethers of polyethylene glycol and cyclic or acyclic alkyl sulfones.

4. The process as claimed in claim 3 wherein said reaction solvent is tetrahydrothiophene-1,1-dioxide.

5. The process as claimed in claim 3 wherein said source of 4-sulfophenyl-[(1-oxyalkanoyl)amino]alkanoate comprises less than about 5% reaction solvent and said ratio of 4-sulfophenyl-[(1-oxyalkanoyl)amino]alkanoate to water ranges from about 1:1 to about 1:40.

6. The process as claimed in claim 1 wherein said water-based purification system further comprises a processing aide.

7. The process as claimed in claim 4 wherein said processing aide is selected from the group consisting of linear or branched $C_2$ to $C_6$ alcohols or diols, linear or branched $C_3$ to $C_6$ ketones, linear or branched $C_3$ to $C_6$ esters, cyclic or acyclic $C_2$ to $C_6$ ethers, linear or branched, cyclic or acyclic $C_1$ to $C_6$ sulfoxides and sulfones and mixtures thereof.

8. The process as claimed in claim 7 wherein said processing aide is selected from the group consisting of ethyl alcohol, propyl alcohol, isopropyl alcohol, acetone and mixtures thereof.

9. The process as claimed in claim 4 wherein said processing aide has a density of less than or equal to that of tetrahydrothiophene-1,1-dioxide.

10. The process as claimed in claim 7 wherein said processing aide is present at a ratio of 4-sulfophenyl-[(1-oxyalkanoyl)amino]alkanoate to processing aide ranging from about 1:0.1 to about 1:50.

11. The process as claimed in claim 10 wherein said processing aide is present at a ratio of 4-sulfophenyl-[(1-oxyalkanoyl)amino]alkanoate to processing aide ranging from about 1:1 to about 1:20.

12. The process as claimed in claim 1 wherein said step of admixing further comprises the step of heating said purification mixture to a temperature of from about 30° C. to about 100° C.

13. The process as claimed in claim 5 wherein said water-based purification system further comprises a processing aide selected from the group consisting of linear or branched $C_2$–$C_6$ alcohols or diols, linear or branched $C_3$–$C_6$ ketones, linear or branched $C_3$ to $C_6$ esters, cyclic or acyclic $C_2$ to $C_6$ ethers, linear or branched, cyclic or acyclic $C_1$ to $C_6$ sulfoxides and sulfones and mixtures thereof.

14. A process for preparing a purified salt of 4-sulfophenyl-[(1-oxyalkanoyl)amino]alkanoate comprising the steps of:
(a) reacting a salt of 4-hydroxybenzene sulfonic acid with a carboxylic anhydride in a reaction solvent to form a reaction mixture having a salt of 4-acyloxybenzenesulfonic acid and a carboxylic acid;
(b) adding a [(1-oxyalkanoyl)amino]alkanoic acid and at least one transesterification catalyst to said reaction mixture and heating at a temperature of from about 120° C. to about 220° C. for from about 0.5 to about 10 hours and a pressure sufficient to maintain reflux of said reaction solvent to form a reaction product containing a salt of 4-sulfophenyl-[(1-oxyalkanoyl)amino]alkanoate;
(c) admixing said reaction product with a water-based purification system to form a purification mixture, said water-based purification system having water present at a ratio of 4-sulfophenyl-[(1-oxyalkanoyl)amino]alkanoate to water ranging from about 1:0.05 to about 1:50;
(d) separating a purified salt of 4-sulfophenyl-[(1-oxyalkanoyl)amino]alkanoate from said purification mixture; and
(e) collecting said purified salt of 4-sulfophenyl-[(1-oxyalkanoyl)amino]alkanoate.

15. The process as claimed in claim 14 wherein said ratio of 4-sulfophenyl-[(1-oxyalkanoyl)amino]alkanoate to water ranges from about 1:0.1 to about 1:40.

16. The process as claimed in claim 14 wherein said reaction solvent is a polar aprotic solvent selected from the group consisting of dialkylacetamides, dialkyl sulfoxides, dialkyl ethers of polyethylene glycol and cyclic or acyclic alkyl sulfones.

17. The process as claimed in claim 16 wherein said reaction solvent is tetrahydrothiophene-1,1-dioxide.

18. The process as claimed in claim 17 wherein said ratio of 4-sulfophenyl-[(1-oxyalkanoyl)amino]alkanoate to water ranges from about 1:0.3 to about 1:3.

19. The process as claimed in claim 14 wherein said process further comprises the step of removing said reaction solvent from said reaction product before the addition of said purification system.

20. The process as claimed in claim 19 wherein said ratio of 4-sulfophenyl-[(1-oxyalkanoyl)amino]alkanoate to water ranges from about 1:1 to about 1:40.

21. The process as claimed in claim 14 wherein said water-based purification system further comprises a processing aide.

22. The process as claimed in claim 21 wherein said processing aide is selected from the group consisting of linear or branched $C_2$–$C_6$ alcohols or diols, linear or branched $C_3$–$C_6$ ketones, linear or branched $C_3$ to $C_6$ esters, cyclic or acyclic $C_2$ to $C_6$ ethers, linear or branched, cyclic or acyclic $C_1$ to $C_6$ sulfoxides and sulfones and mixtures thereof.

23. The process as claimed in claim 22 wherein said processing aide is selected from the group consisting of ethyl alcohol, propyl alcohol, isopropyl alcohol, acetone and mixtures thereof.

24. The process as claimed in claim 21 wherein said processing aide has a density of less than or equal to that of tetrahydrothiophene-1,1-dioxide.

25. The process as claimed in claim 21 wherein said processing aide is present at a ratio of 4-sulfophenyl-[(1-oxyalkanoyl)amino]alkanoate to processing aide ranging from about 1:0.1 to about 1:50.

26. The process as claimed in claim 25 wherein said processing aide is present at a ratio of 4-sulfophenyl-[(1-oxyalkanoyl)amino]alkanoate to purification solvent ranging from about 1:1 to about 1:20.

27. The process as claimed in claim 14 wherein said step of admixing further comprises the step of heating said purification mixture to a temperature of from about 30° C. to about 100° C.

28. A process for preparing a purified salt of 4-sulfophenyl-[(1-oxyalkanoyl)amino]alkanoate comprising the steps of:
(a) reacting an alkali metal salt of 4-hydroxybenzene sulfonic acid with a $C_2$ to $C_4$ carboxylic anhydride at a sufficient temperature and time in a reaction solvent to form a reaction mixture having an alkali metal salt of 4-acyloxybenzenesulfonic acid and a $C_2$ to $C_4$ carboxylic acid, wherein the alkali metal salt of 4 hydroxybenezene sulfonic acid and $C_2$ to $C_4$ carboxylic anhydride are present in a mole ratio of 1:1 to 1:40, respectively, and the reaction solvent is present in a weight ratio of 1:1 to 20:1 based on the weight of the alkali metal salt of 4-hydroxybenzene sulfonic acid, provided that excess carboxylic anhydride is removed under reduced pressure from the reaction vessel;
(b) adding a [(1-oxyalkanoyl)amino]alkanoic acid and at least one transesterification catalyst to said reaction mixture and heating at a temperature of from about 120° C. to about 220° C. for from about 0.5 to about 10 hours and a pressure sufficient to maintain reflux of said reaction solvent and to remove the $C_2$ to $C_4$ carboxylic acid from the reaction vessel, to form a reaction product containing a salt of 4-sulfophenyl-[(1-oxyalkanoyl)amino]alkanoate wherein the moles of the [(1-oxyalkanoyl)amino]alkanoic acid added is 0.7 to 5 times the moles of the alkali metal salt of 4-hydroxybenzene sulfonic acid;

(c) admixing said reaction product including reaction solvent and a salt of 4-sulfophenyl-[(1-oxyalkanoyl)amino]alkanoate with a water-based purification system to form a purification mixture, said water-based purification system including a processing ade and having water present at a ratio of 4-sulfophenyl-[(1-oxyalkanoyl)amino]alkanoate to water ranging from about 1:0.05 to about 1:50;

(d) separating a purified salt of 4-sulfophenyl-[(1-oxyalkanoyl)amino]alkanoate from said purification mixture; and (e) collecting said purified salt of 4-sulfophenyl-[(1-oxyalkanoyl)amino]alkanoate.

29. The process as claimed in claim 28 wherein said process further comprises the step of removing said reaction solvent from said reaction product before the addition of said purification system and said ratio of 4-sulfophenyl-[(1-oxyalkanoyl)amino]alkanoate to water ranges from about 1:1 to about 1:40.

30. The process as claimed in claim 14 wherein said a processing aide selected from the group consisting of ethyl alcohol, propyl alcohol, isopropyl alcohol, acetone and mixtures thereof and said processing aide is present at a ratio of 4-sulfophenyl-[(1-oxyalkanoyl)amino]alkanoate to purification solvent ranging from about 1:1 to about 1:20.

31. The process as claimed in claim 28 wherein said reaction solvent is recovered from said purification mixture after the separation of said purified salt of 4-sulfophenyl-[(1-oxyalkanoyl)amino]alkanoate.

* * * * *